(12) United States Patent
Venable et al.

(10) Patent No.: US 9,244,539 B2
(45) Date of Patent: Jan. 26, 2016

(54) TARGET POSITIONING WITH GAZE TRACKING

(71) Applicant: MICROSOFT TECHNOLOGY LICENSING, LLC, Redmond, WA (US)

(72) Inventors: Morgan Kolya Venable, San Francisco, CA (US); Bernard James Kerr, Sausalito, CA (US); Weerapan Wilairat, Sammamish, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 164 days.

(21) Appl. No.: 14/149,756

(22) Filed: Jan. 7, 2014

(65) Prior Publication Data

US 2015/0193018 A1 Jul. 9, 2015

(51) Int. Cl.
*G09G 5/00* (2006.01)
*G06F 3/0346* (2013.01)
*G02B 27/01* (2006.01)
*G06F 3/01* (2006.01)
*G06K 9/00* (2006.01)
(Continued)

(52) U.S. Cl.
CPC ............ *G06F 3/0346* (2013.01); *A61B 3/113* (2013.01); *G02B 27/017* (2013.01); *G02B 27/0172* (2013.01); *G06F 3/012* (2013.01); *G06F 3/013* (2013.01); *G06F 3/038* (2013.01); *G06F 3/04842* (2013.01); *G06K 9/00671* (2013.01); *G02B 2027/014* (2013.01); *G02B 2027/0156* (2013.01); *G02B 2027/0174* (2013.01); *G02B 2027/0178* (2013.01); *G02B 2027/0187* (2013.01); *G06F 2201/805* (2013.01); *G06F 2209/508* (2013.01)

(58) Field of Classification Search
None
See application file for complete search history.

(56) References Cited

U.S. PATENT DOCUMENTS 6,204,828 B1 3/2001 Amir et al.
6,373,961 B1 4/2002 Richardson et al.
(Continued)

FOREIGN PATENT DOCUMENTS

WO 2013125921 A1 8/2013

OTHER PUBLICATIONS

Tobii, "Tobii Gaze Interfaces for Windows 8 Revolutionizes Laptop Interaction", Youtube, https://www.youtube.com/watch?v=3MoGzTdQnX8, Uploaded Jan. 4, 2012, 1 page.

(Continued)

*Primary Examiner* — Adam R Giesy
(74) *Attorney, Agent, or Firm* — Dave Ream; Tom Wong; Micky Minhas

(57) ABSTRACT

Embodiments that relate to positioning a target indicator via a display system are disclosed. For example, one disclosed embodiment provides a method for positioning a target indicator using gaze tracking data having a coarse accuracy from a gaze tracking system of a computing device. Head pose data having a fine accuracy greater than the coarse accuracy is received from a head tracking system. Using the gaze tracking data, an approximate user gaze region within a display region is determined, and the target indicator is displayed at an initial location within the approximate user gaze region. A reposition input from the user is received. In response, subsequently received head pose data is used to calculate an adjusted location for the target indicator. The target indicator is then displayed at the adjusted location.

20 Claims, 10 Drawing Sheets

(51) Int. Cl.
  *G06F 3/038* (2013.01)
  *G06F 3/0484* (2013.01)
  *A61B 3/113* (2006.01)

(56) References Cited

U.S. PATENT DOCUMENTS

| | | |
|---|---|---|
| 6,847,336 B1 | 1/2005 | Lemelson et al. |
| 2001/0035845 A1 | 11/2001 | Zwern |
| 2005/0047629 A1 | 3/2005 | Farrell et al. |
| 2005/0243054 A1 | 11/2005 | Beymer et al. |
| 2009/0196460 A1 | 8/2009 | Jakobs et al. |
| 2010/0253619 A1 | 10/2010 | Ahn |
| 2012/0272179 A1 | 10/2012 | Stafford |
| 2013/0169560 A1 | 7/2013 | Cederlund et al. |
| 2013/0246967 A1 | 9/2013 | Wheeler et al. |
| 2013/0321271 A1 | 12/2013 | Bychkov et al. |
| 2015/0130740 A1* | 5/2015 | Cederlund ............ B60K 37/06 345/173 |

OTHER PUBLICATIONS

Tobii, "Eyesight Controlled Computer: Tobii Rex", Youtube, https://www.youtube.com/watch?v=qBOCNN_2Pql, Uploaded Jan. 7, 2013, 1 page.

Umoove, "Umoove's Amazing Eye Tracking Technology on Mobile Devices", Youtube, https://www.youtube/com/watch?v=P5hkdu3xnzg, Uploaded Mar. 12, 2013, 1 page.

Umoove, "Umoove Powered by You", Umoove, http://umoove.me, Accessed: Apr. 2, 2014, 1 page.

Wang, J. et al., "Tracking a Head-Mounted Display in a Room-Sized Environment with Head-Mounted Cameras", In Proceedings of SPIE, vol. 1290, Oct. 1, 1990, 11 Pages.

ISA European Patent Office, International Search Report and Written Opinion issued in PCT/US2014/069870, Mar. 25, 2015, Netherlands, 18 Pages.

* cited by examiner

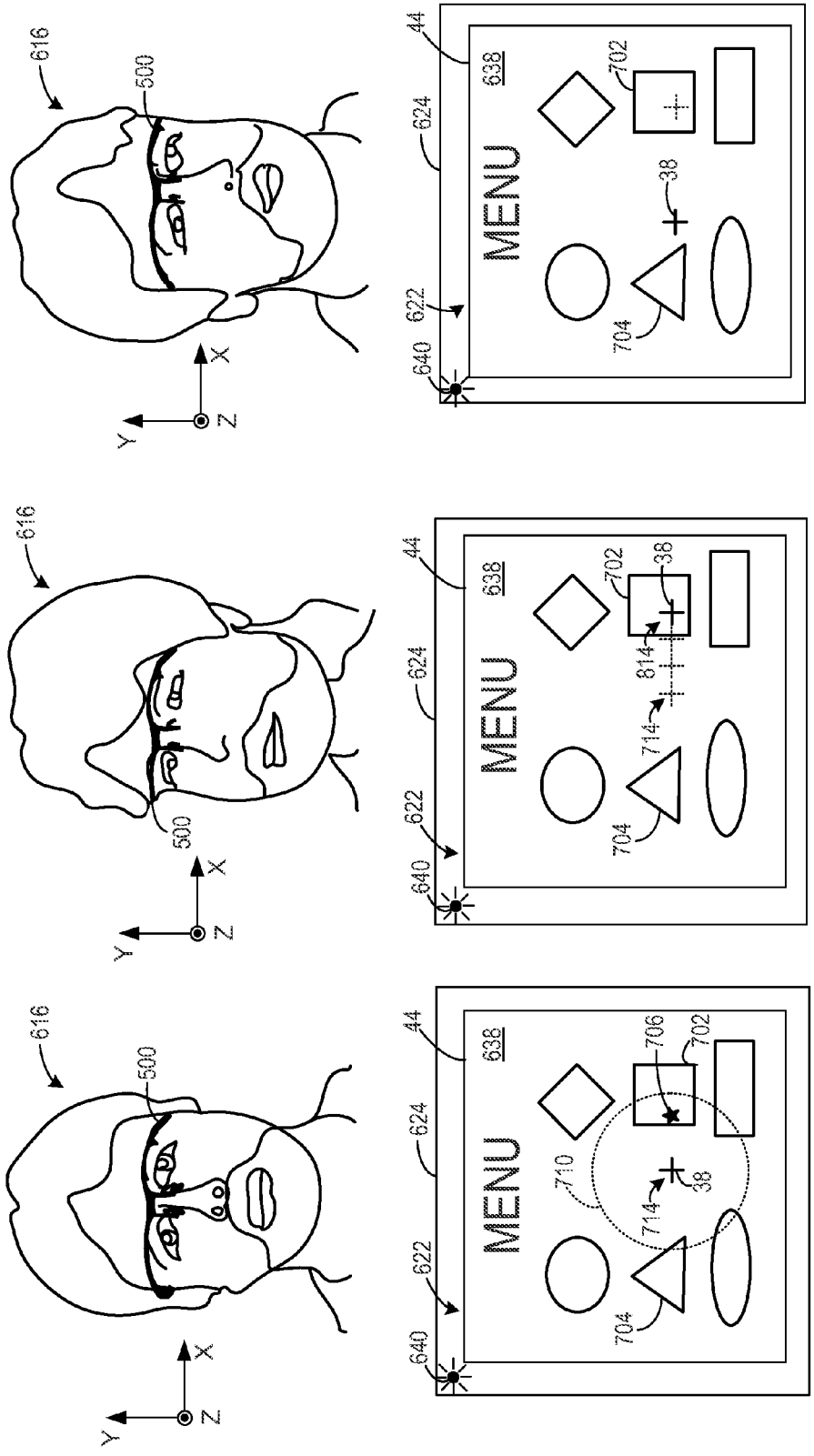

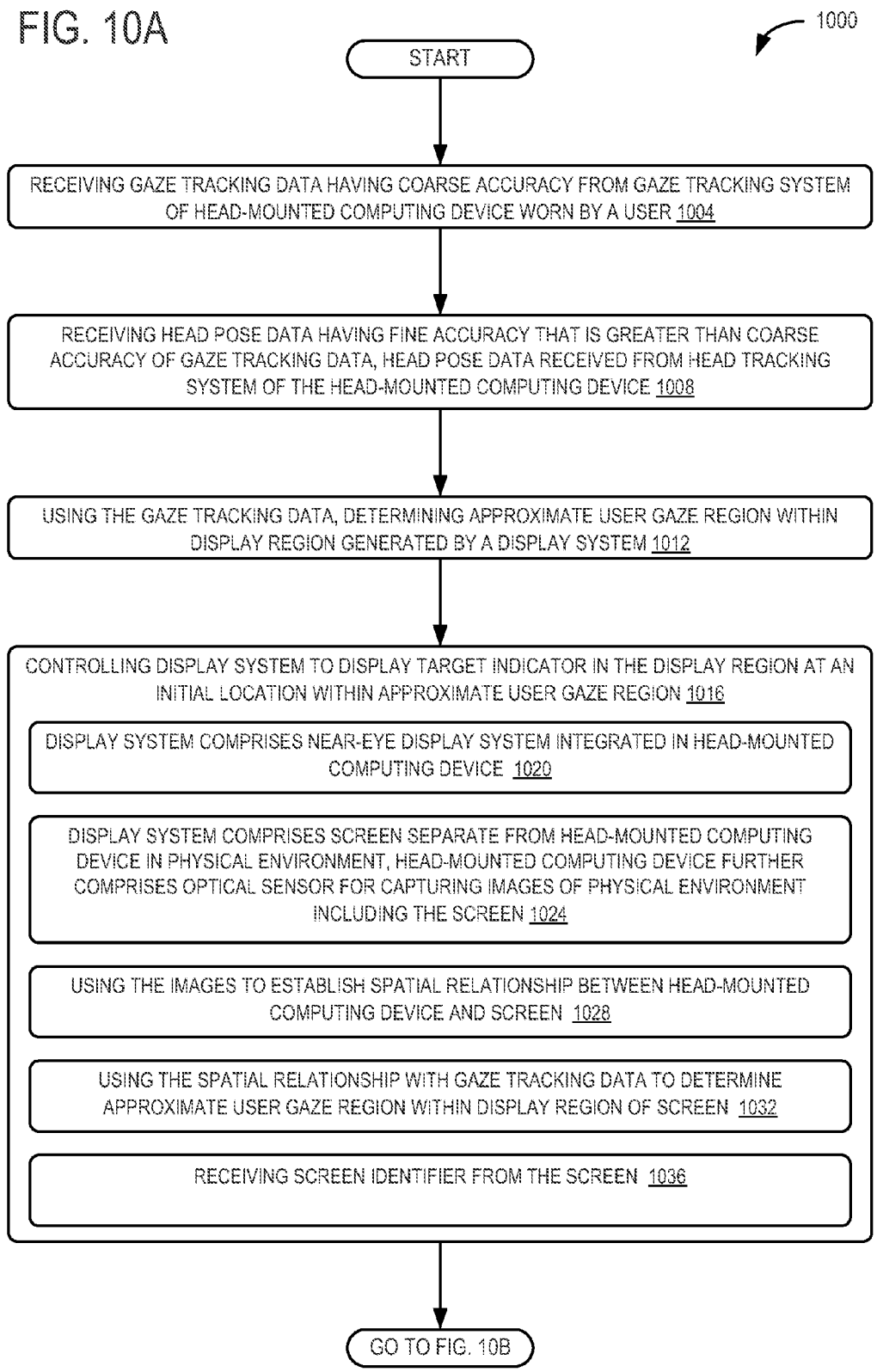

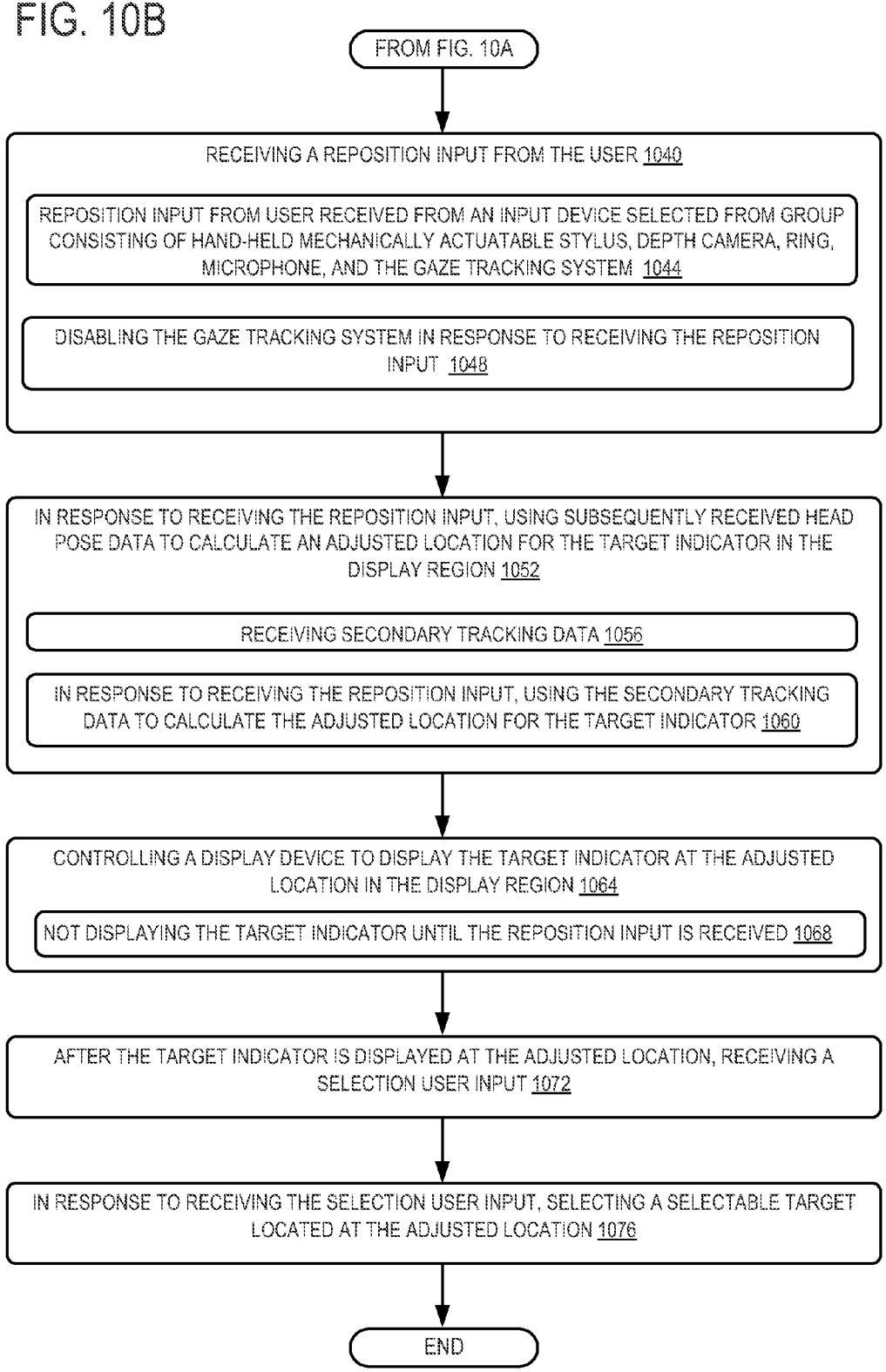

TARGET POSITIONING WITH GAZE TRACKING

BACKGROUND

Navigating electronic content to find and select relevant portions of the content is an often-performed task. In some examples, a gaze tracking system and associated eye-gaze interface may enable a user to navigate among content items that are displayed to the user via a display device. Some of the content items may be selectable by the user via an input device, such as a mouse, keyboard or other mechanism.

Such gaze tracking systems, however, may have limited accuracy and resolution. These limitations may negatively impact a user experience with an eye-gaze interface. For example, where selectable content items are displayed in a smaller size, effective interaction via an eye-gaze interface with limited accuracy may prove challenging. In some cases, where two or more selectable content items are displayed close together and in a small size, navigating to and selecting a desired item with an eye-gaze interface may be difficult or practically impossible. To address this concern, some eye-gaze interfaces may provide display zoom modes and input controls that momentarily enlarge a portion of the displayed content items to facilitate selection.

However, using such special modes to enlarge content items entails additional steps and corresponding user input to ready the display and the desired item for selection. It follows that using such modes undesirably increases the delay between the user forming an intention to select an item and the actual selection of the item.

SUMMARY

Various embodiments are disclosed herein that relate to systems and methods for positioning a target indicator. For example, one disclosed embodiment provides a method for positioning a target indicator via a display system. Gaze tracking data having a coarse accuracy is received from a gaze tracking system of a computing device. Head pose data having a fine accuracy that is greater than the coarse accuracy of the gaze tracking data is received from a head tracking system of the computing device.

Using the gaze tracking data, an approximate user gaze region within a display region generated by the display system is determined. The display system is controlled to display the target indicator in the display region at an initial location within the approximate user gaze region. A reposition input from the user is received. In response, subsequently received head pose data is used to calculate an adjusted location for the target indicator in the display region. The display system is then controlled to display the target indicator at the adjusted location in the display region.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIGS. 7, 8 and 9 are schematic views showing a user's head pose movement and corresponding adjusted locations of a target indicator.

FIGS. 10A and 10B are a flow chart of a method for positioning a target indicator displayed via a display system according to an embodiment of the present disclosure.

DETAILED DESCRIPTION

Figure 1:
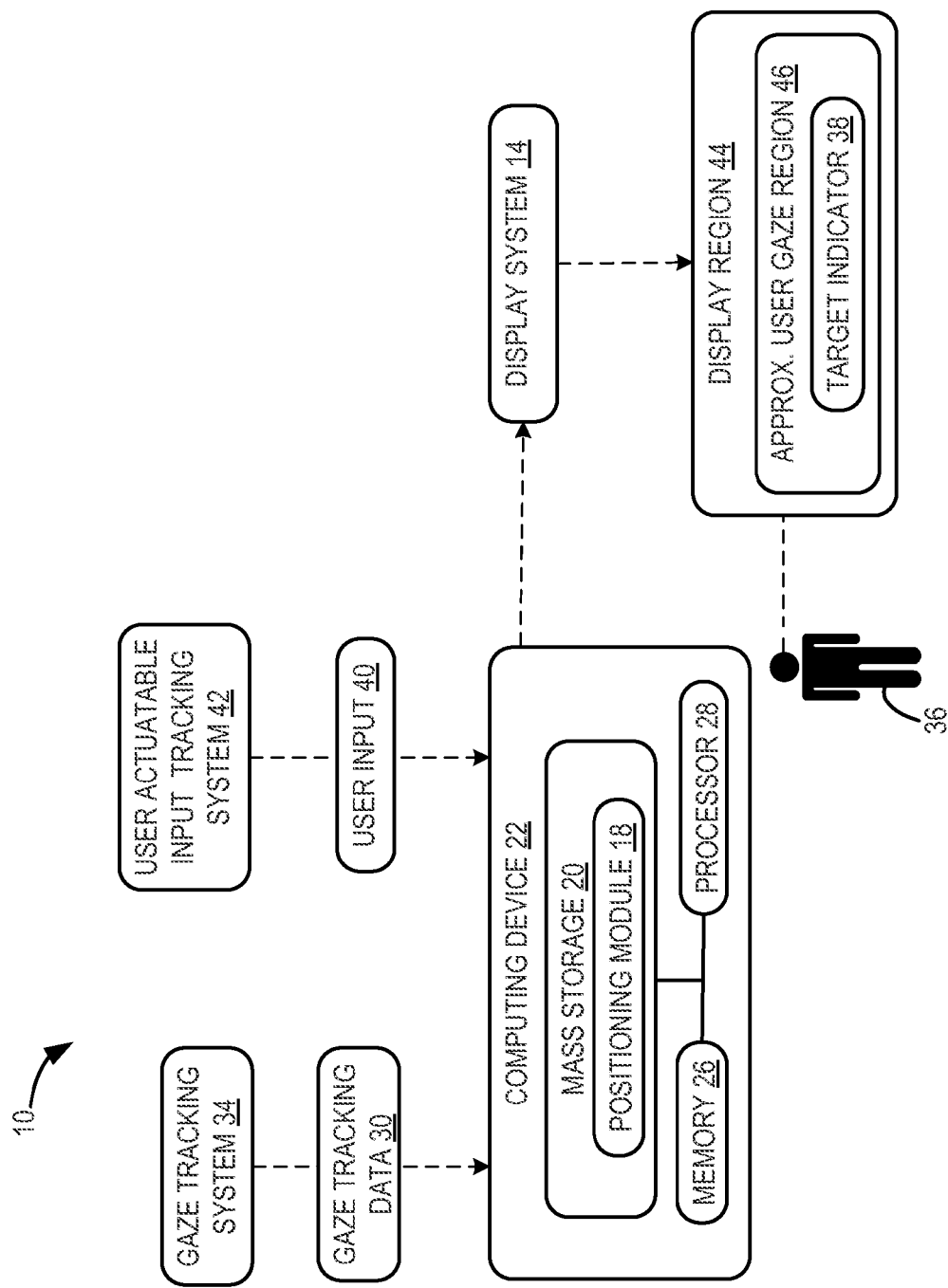
FIG. 1 is a schematic view of a user interface system for positioning a target indicator according to an embodiment of the present disclosure.

FIG. 1 shows a schematic view of one embodiment of a user interface system 10 for positioning a target indicator that is displayed via a display system 14. The user interface system 10 includes a positioning module 18 that may be stored in mass storage 20 of a computing device 22. The positioning module 18 may be loaded into memory 26 and executed by a processor 28 of the computing device 22 to perform one or more of the methods and processes described in more detail below.

The computing device 22 may receive gaze tracking data 30 from a gaze tracking system 34 and user input 40 from a user actuatable input tracking system 42. As described in more detail below, in various embodiments the gaze tracking system 34 may be located in a head-mounted computing device with or without an integrated display, a tablet, notebook, smartphone, or other mobile computing device, desktop computing device, standalone monitor, wall-mounted display, interactive whiteboard, gaming console, keyboard, dedicated peripheral, or other suitable device. Similarly, the user actuatable input tracking system 42 may be located in a head-mounted computing device or other wearable computing device with or without an integrated display, hand-held user input device, tablet, notebook, smartphone, or other mobile computing device, desktop computing device, standalone monitor, wall-mounted display, interactive whiteboard, gaming console, keyboard, dedicated peripheral, or other suitable device. The user actuatable input tracking system 42 may comprise, for example, a head tracking system, an optical camera, a depth camera, a hand-held user input device, or other suitable device.

The user interface system 10 may include a display system 14 for presenting one or more visual elements to a user 36. As described in more detail below, the positioning module 18 may utilize gaze tracking data 30 to control the display system 14 to display a target indicator 38 within a display region 44 at a location corresponding to an approximate user gaze region 46. Advantageously, the positioning module 18 may also utilize user input 40 in the form of head tracking data to refine the positioning of the target indicator 38. Using such data, the positioning module 18 may control the display system 14 to display the target indicator 38 at adjusted locations.

A "target indicator" refers to a pointer or other indicator that is associated with a computer program and denotes a focus of the computer program. As described in more detail below, the target indicator may refer to an estimated user gaze location which is shown on a display. The target indicator may be represented on screen in different forms, such as crosshairs, an arrow, a hand, a finger, a vertical bar, a scroll bar, etc. The target indicator may also be hidden at times, making the indictor implicit but still available to perform some interface operations. Embodiments are presented using a particular form of target indicator, but it will be appreciated that any type of target indictor can be utilized.

As shown in FIG. 1, the display system 14 is operatively connected to computing device 22. In some examples, the display system 14 may comprise a separate display, such as a standalone monitor, wall-mounted display, etc., that is operatively connected to computing device 22 via a wired or wireless connection. In other examples, the computing device 22 and the display system 14 may be integrated into a shared enclosure. Such examples may include, for example, standalone monitors, wall-mounted displays, head-mounted display devices, hand-held smart phones, e-readers, laptop, notebook and tablet computers, etc. It will be appreciated that many other types and configurations of display systems having various form factors, whether separate from or integrated with computing device 22, may also be used and are within the scope of the present disclosure.

Figure 2:
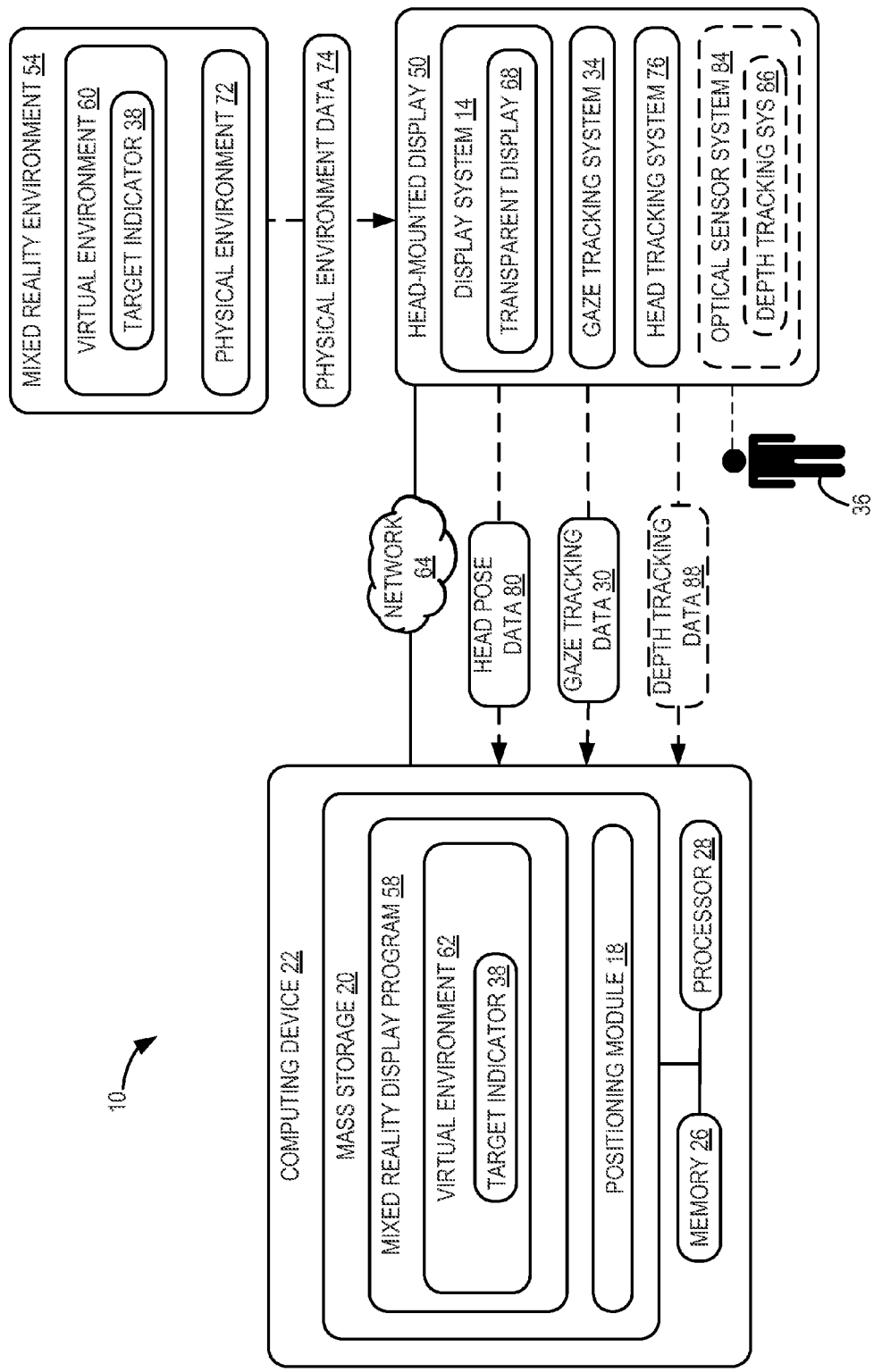
FIG. 2 is a schematic view of a head-mounted computing device in the form of a head-mounted display device including a near-eye display for positioning a target indicator according to an embodiment of the present disclosure.

In some examples and with reference now to FIG. 2, the display system 14 may be integrated into a head-mounted computing device in the form of a near-eye display system, such as head-mounted display (HMD) device 50 or other wearable virtual or mixed-reality capable device. As explained in more detail below, the HMD device 50 may create a mixed reality environment 54. In these examples, the user interface system 10 may include a mixed reality display program 58 that may generate a virtual environment 60 for display via HMD device 50. The virtual environment 60 may include one or more visual elements in the form of virtual images, such as three-dimensional (3D) holographic objects and two-dimensional (2D) virtual images, that are generated and displayed via HMD device 50. The visual elements may include the target indicator 38.

The computing device 22 may be operatively connected with the HMD device 50 using a wired connection, or may employ a wireless connection via WiFi, Bluetooth, or any other suitable wireless communication protocol. For example, the computing device 22 may be communicatively coupled to a network 64. The network 64 may take the form of a local area network (LAN), wide area network (WAN), wired network, wireless network, personal area network, or a combination thereof, and may include the Internet. Additionally, the example illustrated in FIG. 2 shows the computing device 22 as a separate component from the HMD device 50. It will be appreciated that in other examples the computing device 22 may be integrated into the HMD device 50.

The computing device 22 may take the form of a desktop computing device, a mobile computing device such as a smart phone, laptop, notebook or tablet computer, network computer, home entertainment computer, interactive television, gaming system, or other suitable type of computing device. Additional details regarding the components and computing aspects of the computing device 22 are described in more detail below with reference to FIG. 11.

Figure 3:
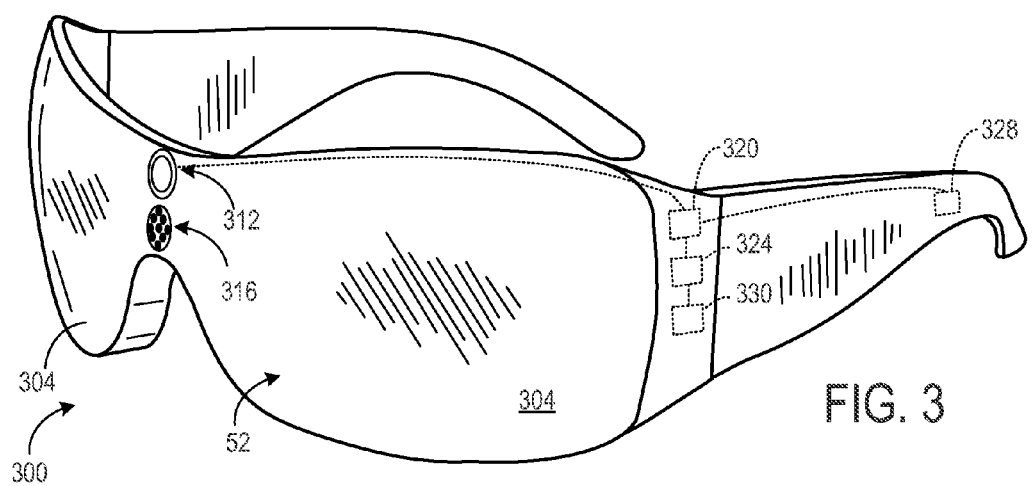
FIG. 3 shows an example head-mounted display device with a near-eye display according to an embodiment of the present disclosure.

With reference now also to FIG. 3, one example of an HMD device 300 in the form of a pair of wearable glasses with a transparent display 68 is provided. It will be appreciated that in other examples, the HMD device 300 may take other suitable forms in which a transparent, semi-transparent or non-transparent display is supported in front of a viewer's eye or eyes. It will also be appreciated that the HMD device 50 shown in FIG. 2 may take the form of the HMD device 300, as described in more detail below, or any other suitable HMD device.

The HMD device 50 includes a display system 14 and transparent display 68 that enables images such as holographic objects to be delivered to the eyes of a user 36. The transparent display 68 may be configured to visually augment an appearance of a physical environment 72 to user 36 viewing the physical environment through the transparent display. For example, the appearance of the physical environment 72 may be augmented by graphical content (e.g., one or more pixels each having a respective color and brightness) that is presented via the transparent display 68 to create the mixed reality environment 54.

The transparent display 68 may also be configured to enable a user to view a physical, real-world object in the physical environment 72 through one or more partially transparent pixels that are displaying a virtual object representation. As shown in FIG. 3, in one example the transparent display 68 may include image-producing elements located within lenses 304 (such as, for example, a see-through Organic Light-Emitting Diode (OLED) display). As another example, the transparent display 68 may include a light modulator on an edge of the lenses 304. In this example the lenses 304 may serve as a light guide for delivering light from the light modulator to the eyes of a user. Such a light guide may enable a user to perceive a 3D holographic image located within the physical environment 72 that the user is viewing, while also allowing the user to view physical objects in the physical environment, thus creating a mixed reality environment.

The HMD device 50 may also include various sensors and related systems. For example, the HMD device 50 may include a gaze tracking system 34 that includes one or more image sensors configured to acquire image data in the form of gaze tracking data 30 from a user's eyes. Provided the user has consented to the acquisition and use of this information, the gaze tracking system 34 may use this information to track a position and/or movement of the user's eyes.

In one example, the gaze tracking system 34 includes a gaze detection subsystem configured to detect a direction of gaze of each eye of a user. The gaze detection subsystem may be configured to determine gaze directions of each of a user's eyes in any suitable manner. For example, the gaze detection subsystem may comprise one or more light sources, such as infrared light sources, configured to cause a glint of light to reflect from the cornea of each eye of a user. One or more image sensors may then be configured to capture an image of the user's eyes.

Images of the glints and of the pupils as determined from image data gathered from the image sensors may be used to determine an optical axis of each eye. Using this information, the gaze tracking system 34 may then determine a direction and/or at what location, physical object, and/or virtual object the user is gazing. The gaze tracking system 34 may further determine at what location on a physical or virtual object the user is gazing. Such gaze tracking data 30 may then be provided to the computing device 22.

As noted above, gaze tracking systems may have limited detection resolutions and correspondingly limited accuracy in determining an actual gaze location of a user. For example, hardware and/or software limitations may limit the accuracy of a gaze tracking system. It will also be appreciated that the human eye undergoes natural, involuntary movements such as, for example, saccades, microsaccades, jitter, tremors, and drifts. Such natural movements may also impact an accuracy of a gaze tracking system. Accordingly, gaze tracking data generated by such systems may have a relatively coarse accuracy with respect to the actual gaze location of a user.

It will also be understood that the gaze tracking system 34 may have any suitable number and arrangement of light sources and image sensors. For example and with reference to FIG. 3, the gaze tracking system 34 of the HMD device 300 may utilize at least one inward facing sensor 312.

The HMD device 50 may also include sensor systems that receive physical environment data 74 from the physical environment 72. For example, the HMD device 50 may also include a head tracking system 76 that utilizes one or more motion sensors, such as motion sensors 320 on HMD device 300, to capture head pose data 80 and thereby enable position tracking, direction and orientation sensing, and/or motion detection of the user's head. Additionally, such head pose data 80 may have a fine accuracy that is greater than the coarse accuracy of the gaze tracking data 30. Accordingly and as described in more detail below, the positioning module 18 may receive head pose data 80 as user input that enables a user 36 to conveniently and smoothly fine-tune the location of a target indicator 38 via head movements.

In one example, head tracking system 76 may comprise an inertial measurement unit configured as a three-axis or three-degree of freedom position sensor system. This example position sensor system may, for example, include three gyroscopes to indicate or measure a change in orientation of the HMD device 50 within 3D space about three orthogonal axes (e.g., x, y, z) (e.g., roll, pitch, yaw). In another example, head tracking system 76 may comprise an inertial measurement unit configured as a six-axis or six-degree of freedom position sensor system. This example position sensor system may, for example, include three accelerometers and three gyroscopes to indicate or measure a change in location of the HMD device 50 along the three orthogonal axes and a change device orientation about the three orthogonal axes.

Head tracking system 76 may also support other suitable positioning techniques, such as GPS or other global navigation systems. Further, while specific examples of position sensor systems have been described, it will be appreciated that any other suitable position sensor systems may be used.

In some examples the HMD device 50 may also include an optical sensor system 84 that utilizes one or more outward facing sensors, such as optical sensor 316 on HMD device 300, to capture image data. The outward facing sensor(s) may detect movements within its field of view, such as gesture-based inputs or other movements performed by a user 36 or by a person or physical object within the field of view. The outward facing sensor(s) may also capture 2D image information and depth information from physical environment 72 and physical objects within the environment. For example, the outward facing sensor(s) may include a depth camera, a visible light camera, an infrared light camera, and/or a position tracking camera.

The optical sensor system 84 may include a depth tracking system 86 that generates depth tracking data 88 via one or more depth cameras. In one example, each depth camera may include left and right cameras of a stereoscopic vision system. Time-resolved images from one or more of these depth cameras may be registered to each other and/or to images from another optical sensor such as a visible spectrum camera, and may be combined to yield depth-resolved video.

In other examples a structured light depth camera may be configured to project a structured infrared illumination, and to image the illumination reflected from a scene onto which the illumination is projected. A depth map of the scene may be constructed based on spacings between adjacent features in the various regions of an imaged scene. In still other examples, a depth camera may take the form of a time-of-flight depth camera configured to project a pulsed infrared illumination onto a scene and detect the illumination reflected from the scene. It will be appreciated that any other suitable depth camera may be used within the scope of the present disclosure.

The outward facing sensor(s) may capture images of the physical environment 72 in which a user 36 is situated. With respect to the HMD device 50, in one example the mixed reality display program 58 may include a 3D modeling system that uses such captured images to generate a virtual environment 60 that models the physical environment 72 surrounding the user 36.

The HMD device 50 may also include a microphone system that includes one or more microphones, such as microphone 324 on HMD device 300, that capture audio data. In other examples, audio may be presented to the user via one or more speakers, such as speaker 328 on the HMD device 300.

The HMD device 50 may also include a processor, such as processor 330 on the HMD device 300. The processor includes a logic subsystem and a storage subsystem, as discussed in more detail below with respect to FIG. 11, that are in communication with the various sensors and systems of the HMD device and display. In one example, the storage subsystem may include instructions that are executable by the logic subsystem to receive signal inputs from the sensors and forward such inputs to computing device 22 (in unprocessed or processed form), and to present images to a user via the HMD device 300.

Figure 4:
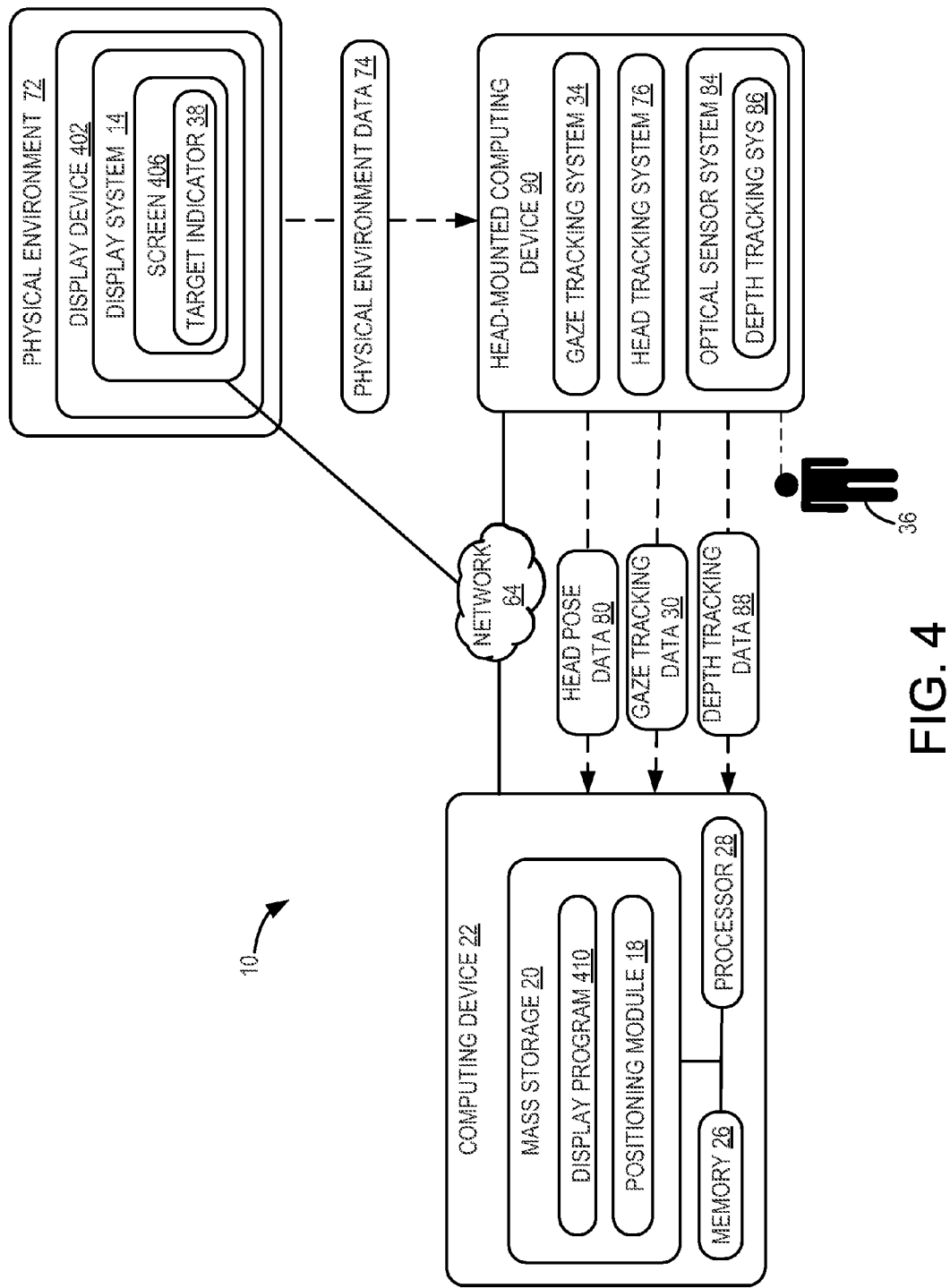
FIG. 4 is a schematic view of a head-mounted computing device for positioning a target indicator according to another embodiment of the present disclosure.

As noted above, in other examples and with reference now to FIG. 4, the display system 14 may be integrated into a separate display device 402, such as a standalone monitor, wall-mounted display, etc., that is not worn by the user 36. In these examples, the user 36 may wear a head-mounted computing (HMC) device 90 that does not include a display system. Instead, the separate display device 402 comprises a display system 14 that includes a screen 406 for displaying images and other content items including a target indicator 38. In these examples, the user interface system 10 may include a display program 410 that may generate the visual content items for display via the display device 402. Advantageously, and as described in more detail below, using the HMC device 90 the user 36 may provide user input 40 via gaze tracking data 30, head pose data 80 and/or depth tracking data 88 to conveniently and precisely navigate the target indicator 38 on the screen 406.

The computing device 22 may be operatively connected with the HMC device 90 and display device 402 using a wired connection, or may employ a wireless connection via WiFi, Bluetooth, or any other suitable wireless communication protocol. For example, the computing device 22, HMC device 90 and display device 402 may be communicatively coupled via network 64. Additionally, the example illustrated in FIG. 4 shows the computing device 22 as a separate component from the HMC device 90 and display device 402. It will be appreciated that in other examples the computing device 22 may be integrated into HMC device 90 or into the display device 402 in a shared enclosure.

The HMC device 90 may include a gaze tracking system 34, head tracking system 76, and optical sensor system 84 including a depth tracking system 86 as described above.

Figure 5:
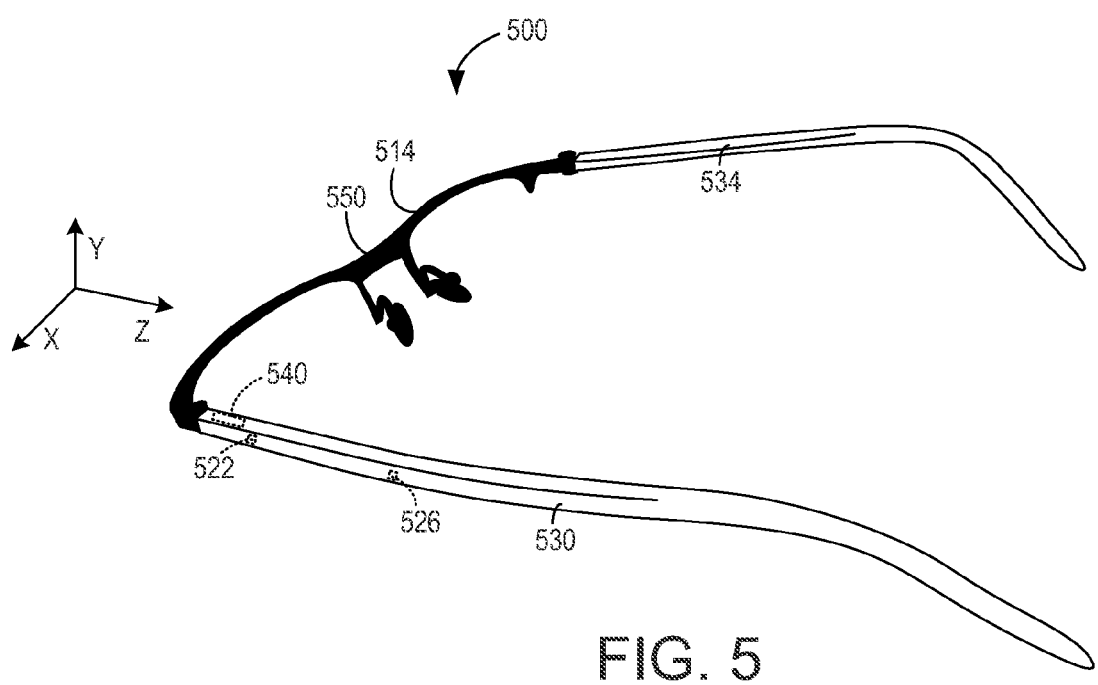
FIG. 5 shows an example head-mounted computing device without an integrated display according to an embodiment of the present disclosure.

With reference now also to FIG. 5, one example of an HMC device 90 in the form of a pair of wearable eyeglass frames 500 is illustrated. It will also be appreciated that many other types and configurations of wearable HMC devices having various form factors may also be used within the scope of the present disclosure.

In this example, the head tracking system 76 of the eyeglass frames 500 includes a first two-axis accelerometer 522 and a second two-axis accelerometer 526 to indicate or measure a change in location of the HMC device within two-dimensional space along two orthogonal axes (e.g., x and y). For example, each accelerometer may measure translation along or rotation about the two orthogonal axes.

It will be appreciated that this example configuration of accelerometers is provided for descriptive purposes, and that other configurations of one or more motions sensors may also be utilized to generate head pose data 80. For example, one or more three-axis accelerometers may be utilized to measure a change in location or orientation of the eyeglass frames 500. In other examples, one or more gyroscopes may be utilized to determine three-axis orientation around the x, y and z axes.

In other examples the eyeglass frames 500 may also include other suitable positioning components, such as a compass, global positioning system (GPS) or other navigation systems. The eyeglass frames 500 may also include one or more microphones to determine sound direction data, which may be used to enhance the determination of relative motion of the eyeglasses.

As noted above, the eyeglass frames 500 may also include various other sensors and related systems. For example, the eyeglass frames 500 may include one or more optical sensor(s) that may capture image data. In some examples the one or more optical sensor(s) may include an outwardly-facing sensor, such as a camera (not shown) facing away from the user's head and located at a nose bridge portion 550 of a display bridge 514 of the eyeglasses. The camera may capture two-dimensional image information and/or depth information from the physical environment 72 and physical objects within the environment of the user 36 as described above.

It will be appreciated that the HMC device 90, eyeglass frames 500 and related sensors and other components described above and illustrated in FIGS. 4 and 5 are provided by way of example. These examples are not intended to be limiting in any manner, as any other suitable sensors, components, and/or combination of sensors and components may be utilized. Therefore it is to be understood that the HMC device 90 and eyeglass frames 500 may include additional and/or alternative sensors, cameras, microphones, input devices, output devices, etc. without departing from the scope of this disclosure. Further, the physical configuration of the HMC device 90, eyeglass frames 500 and various sensors and subcomponents may take a variety of different forms without departing from the scope of this disclosure.

Figure 6:
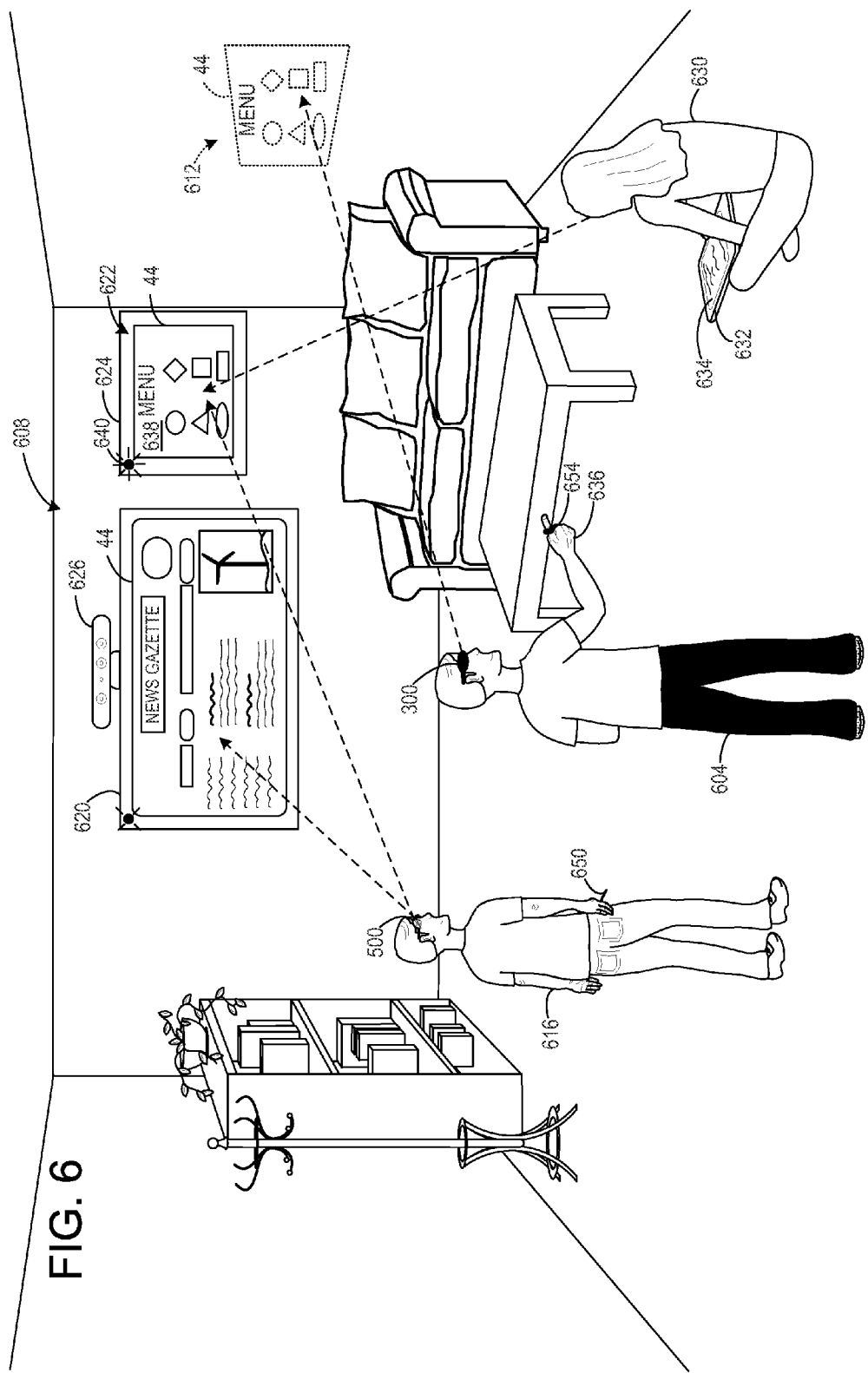
FIG. 6 is a schematic perspective view of a room including a user holding a tablet computer, a user wearing the head-mounted display device of FIG. 3, and a user wearing the head-mounted computing device of FIG. 5.

With reference now to FIGS. 6-9, descriptions of example use cases and embodiments of the user interface system 10, HMD device 50 and HMC device 90 will now be provided. FIG. 6 provides a schematic illustration of a first user 604 located in a physical environment that comprises a family room 608. The first user 604 is wearing the HMD device 300 described above and is viewing a virtual menu 612 with selectable targets via the HMD device.

A second user 616 is wearing the eyeglass frames 500 described above and is alternately viewing a first wall-mounted display 620 that is displaying a news website with selectable targets and a second wall-mounted display 624 displaying a menu 622 with selectable targets. The first wall-mounted display 620 also may be operatively connected to a gaming system 626. The gaming system 626, first wall-mounted display 620 and/or second wall-mounted display 624 may include user interface system 10 and a gaze tracking system 34 and head tracking system 76 as described above. A third user 630 is shown holding a computing device in the form of a touch screen tablet computer 632 that may include a gaze tracking system 34 and head tracking system 76 as described above. The third user 630 is also viewing the second wall-mounted display 624.

With reference now to FIGS. 7-9, schematic views of one example of adjusting the position of a target indicator 38 with respect to a plurality of visual elements that are displayed in a display region 44 are provided. In this example, the visual elements comprise various selectable targets, such as square item 702, triangle item 704, etc. For purposes of the present example, the display region 44 will be described as the screen 638 of the second wall-mounted display 624 shown in FIG. 6.

It will also be appreciated that the principles of the present example may apply to other configurations of the user interface system 10 and other display devices and HMC devices discussed above, such as the first wall-mounted display 620, the tablet computer 632, the HMD device 300 generating virtual menu 612, and the eyeglass frames 500. Further, it will be appreciated that the principles of the present disclosure may apply to a variety of content displayed via a display system 14 including, but not limited to, web pages, user interface graphics, video game graphics, streaming content including movies, video calls or chats, online meetings, presentations and other interactive collaborations, two-dimensional and three-dimensional holographic images, and any other suitable content displayed via a display system 14.

In one example, the second user 616 wearing eyeglass frames 500 may look at the menu 622 displayed in the display region 44 of the second wall-mounted display 624. More particularly and with reference also to FIG. 7, the second user 616 may desire to select the selectable square item 702, and may initially focus his gaze on an actual gaze location 706, indicated by a star, in the lower left point on the square 702. It will be appreciated that this actual gaze location is not displayed to the user.

With reference again to FIG. 6, in one example the optical sensor system 84 of the eyeglass frames 500 may capture images of the room 608 including images of the second wall-mounted display 624. Using these images along with depth tracking data from the depth tracking system 86, the positioning module 18 may establish a spatial relationship between the eyeglass frames 500 and the screen 638 of the second wall-mounted display 624. Such spatial relationship along with gaze tracking data 30 from the gaze tracking system 34 may be utilized by the positioning module 18 to enable the second user 616 to interact with the second wall-mounted display 624, as described in more detail below.

Additionally, it will be appreciated that the above-described configuration may enable a user to interact with any one of multiple display screens that may be located in the vicinity of the user. For example, such a configuration may enable the second user 616 to interact with the first wall-mounted display 620 in the room 608, by simply looking at the first wall-mounted display.

To communicatively couple the eyeglass frames 500 to a display screen at which the second user 616 is gazing, in some examples a display screen may also communicate a screen identifier. For example, the second wall-mounted display 624 may include an infrared LED beacon 640 that may broadcast an identifying pattern via sequenced infrared flashes that are captured by the optical sensor system 84 of the eyeglass frames 500. In another example, the second wall-mounted display 624 may display a glyph or other identifying pattern that may be similarly captured by the optical sensor system 84 of the eyeglass frames 500. It will be appreciated that any suitable screen identifier may be utilized to communicatively couple the eyeglass frames 500 with the display screen. Additionally, such screen identifier may not be visible to a user.

With reference again to FIG. 7, when the second user 616 fixes his gaze at actual gaze location 706, the user may provide a reposition input to the positioning module 18. In response to receiving the reposition input, the positioning module 18 may control a display system 14 of the second wall-mounted display 624 to display a target indicator 38 in the display region 44 at an initial location 714 with an approximate user gaze region 710.

As described in more detail below, the approximate user gaze region 710 is determined via the gaze tracking data 30. In the present example, the target indicator 38 is shown as a crosshairs icon. It will be appreciated that any suitable form of target indicator 38 may also be used. Additionally, in some examples and to avoid unnecessary user distraction, the target indicator 38 is not displayed until the reposition input is received from the user. In other examples, the target indicator 38 may be continuously displayed.

As described in more detail below, and also in response to receiving the reposition input, the positioning module 18 may utilize subsequently received head pose data 80 from the head tracking system 76 of the eyeglass frames 500 to adjust the location of the target indicator 38 in the display region 44. In some examples and also in response to receiving the reposition input, the positioning module 18 may disable the gaze tracking system 34. Advantageously, in this manner power, battery life, and/or computational resources of the corresponding computing device that would otherwise be consumed by the gaze tracking system 34 may be preserved.

Additionally, with the gaze tracking system 34 disabled, user positioning of the target indicator 38 may be accomplished solely by head movement of the second user 616 and corresponding head pose data 80. Advantageously, the second user 616 may thereby conveniently and accurately reposition the target indicator 38 to a desired location within the display region 44.

The reposition input may be provided by the user via any suitable user input device. In one example and with reference again to FIG. 6, the second user 616 may utilize a hand-held mechanically actuatable stylus 650 to provide reposition input. For example, the stylus may include a two-stage button on a body of the stylus that enables the user to provide a first input, such as a reposition input, upon pressing the button, and a second, different input, such as a selection input, upon releasing the button.

In other examples and other configurations of the user interface system 10, the user input device may comprise a depth camera that may detect a user's reposition input in the form of a predetermined gesture performed by the user. In other examples and with reference again to FIG. 6, the user input device may comprise a wearable input device, such as a ring 654. In this example, the first user 604 may wear the ring 654 on the user's index finger, and may actuate a button on the ring with the user's thumb to provide the reposition input. In another example, the ring 654 may include one or more touch-sensitive surfaces with which the user may provide reposition input and other user inputs.

In other examples, the user input device may comprise a microphone on the eyeglass frames 500 that may receive a reposition input in the form of a voice command from the second user 616. In other examples, the user input device may comprise the gaze tracking system 34 of the eyeglass frames 500. For example, the positioning module 18 may be configured to recognize a predetermined eye movement by the user, such as three quick blinks or other pattern, as a reposition input. It will also be appreciated that other suitable user input devices may also be utilized.

In the example in FIG. 7, the approximate user gaze region 710 is illustrated as a circle. It will be appreciated that in other examples, other shapes and/or sizes of an approximate user gaze region 710 may be utilized. The configuration of an approximate user gaze region 710 may relate to the resolution, accuracy, and/or other aspects of a particular gaze tracking system configuration. In some examples, the approximate user gaze region 710 is not displayed to the user. In other examples, the approximate user gaze region 710 may be displayed to the user.

As noted above, gaze tracking systems may have limited detection resolutions and correspondingly limited accuracy in determining an actual gaze location of a user. In the example of FIG. 7, the gaze tracking data 30 may yield an approximate user gaze region 710 in the form of a circle having a diameter of 50 mm., which corresponds to the limits of the coarse accuracy of the gaze tracking data generated by the gaze tracking system 34. It will be appreciated that in different examples and embodiments, the coarse accuracy of the gaze tracking data 30 may have a variety of different values that are related to the particular components and capabilities of a given gaze tracking system 34, as well as other factors such as a distance of a user from the user gaze region 710, ambient lighting conditions, etc.

Using the approximate user gaze region 710, the positioning module 18 may estimate the location of the actual gaze location of the user within the approximate user gaze region 710. In the present example, the positioning module 18 may estimate the actual gaze location to be at the approximate center of the user gaze region 710. Using this estimate, the positioning module 18 may control the display system 14 to display the target indicator 38 in the display region 44 at the initial location 714 which corresponds to the approximate center of the user gaze region 710. It will also be appreciated that any suitable method or algorithm for estimating an actual gaze location within a user gaze region may be utilized.

With reference now to FIGS. 7 and 8 and in response to receiving the reposition input, the positioning module 18 may utilize subsequently received head pose data 80 from the head tracking system 76 of the eyeglass frames 500 to calculate an adjusted location for the target indicator 38. As noted above, the head tracking system 76 may generate head pose data 80 having a fine accuracy that is greater than the coarse accuracy of the gaze tracking data 30.

Advantageously, and once the target indicator 38 is displayed, the second user 616 may conveniently and precisely adjust the location of the target indicator by moving the user' head and generating head pose data 80 via the head tracking system 76. In one example, a 1 degree rotation of a user's head may cause a 1 mm translation of the target indicator 38 in the display region 44. Thus in these examples, whereas the coarse accuracy of the gaze tracking data 30 yields a 50 mm. diameter circle in which the target indicator may be displayed, the fine accuracy of the head pose data 80 enables to user to more precisely position the target indicator at 1 mm increments. It will also be appreciated that that in different examples and embodiments, the fine accuracy of the head pose data 80 may have a variety of different values that are related to the particular components and capabilities of a given head tracking system 76 as well as other factors.

With reference again to FIG. 7, and with the user's gaze at actual gaze location 706, the second user 616 may provide user input 40 in the form of head pose data 80 to adjust the location of the target indicator 38 toward the selectable square item 702. More particularly and as shown in FIG. 8, the second user 616 may rotate his head to the user's right (clockwise about the y-axis) and in response, the positioning module 18 may control the second wall-mounted display 624 to the move the target indicator 38 from its initial location 714 to an adjusted location 814. Thus, by slightly turning his head to the right, the second user 616 may conveniently and smoothly move the target indicator 38 from its initial location 714, which did not correspond to the user's actual gaze location 706 on the selectable square item 702, to an adjusted location 814 over the square item.

With the target indicator now positioned over the selectable square item 702, the second user 616 user may provide a selection user input to select the square item. To provide the selection user input, the second user 616 may use the same input device as the user used to provide the reposition input. For example, where the user uses the hand-held mechanically actuatable stylus 650 to provide the reposition input by pressing the button, the selection user input may be provided by the user releasing the button. In other examples and as described above, the selection user input may comprise a voice command, a blinking pattern or other predetermined eye movement, or any other suitable form of input received by a corresponding input device.

As shown in FIG. 9, the second user 616 may similarly move the target indicator 38 from right to left by rotating his head to his left, or counter-clockwise about the y-axis. In a similar manner, the second user 616 may move the target indicator 38 upwardly in the display region 44 by nodding his head upwardly, or clockwise about the x-axis, and may move the target indicator downwardly by nodding his head downwardly, or counter-clockwise about the x-axis.

In some examples, secondary tracking data received from another tracking system or user input device also may be utilized to calculate an adjusted location for the target indicator 38. For example and with reference again to FIG. 6, the third user 630 holding the touch screen tablet computer 632 may be viewing the second wall-mounted display 624. Once the target indicator 38 is displayed, the third user 630 may touch and move her finger on the touch screen 634 of the tablet computer 632 to provide secondary tracking data to the positioning module 18 of the tablet computer. Using this subsequently received secondary tracking data, the positioning module 18 may calculate an adjusted location for the target indictor 38.

In another example, the first user 604 wearing the HMD device 300 and viewing a virtual menu 612 may provide secondary tracking data and/or reposition input via one or more gestures of the user's hand 636 that are captured by the depth tracking system 86 of the HMD device 300. In another example, the second user 616 wearing the eyeglass frames 500 may provide secondary tracking data via one or more motion sensors in the hand-held mechanically actuatable stylus 650.

FIGS. 10A AND 10B illustrate a flow chart of a method 1000 for positioning a target indicator displayed via a display system according to an embodiment of the present disclosure. The following description of method 1000 is provided with reference to the software and hardware components of the user interface system 10, HMD device 50 and HMC device 90 described above and shown in FIGS. 1-9. It will be appreciated that method 1000 may also be performed in other contexts using other suitable hardware and software components.

With reference to FIG. 10A, at 1004 the method 1000 may include method receiving gaze tracking data having a coarse accuracy from a gaze tracking system of a head-mounted computing device worn by a user. At 1008 the method 1000 may include receiving head pose data having a fine accuracy that is greater than the coarse accuracy of the gaze tracking data, with the head pose data being received from a head tracking system of the head-mounted computing device. At 1012 the method 1000 may include, using the gaze tracking data, determining an approximate user gaze region within a display region generated by the display system.

At 1016 the method 1000 may include controlling the display system to display the target indicator in the display region at an initial location within the approximate user gaze region. At 1020 the display system may comprise a near-eye display system integrated in the head-mounted computing device. At 1024 the display system may comprise a screen in a physical environment and separate from the head-mounted computing device, with the head-mounted computing device further comprising an optical sensor for capturing images of the physical environment including the screen.

At 1028 the method 1000 may include using the images to establish a spatial relationship between the head-mounted computing device and the screen. At 1032 the method 1000 may include using the spatial relationship in combination with the gaze tracking data to determine the approximate user gaze region within the display region of the screen. At 1036 the method 1000 may include receiving a screen identifier from the screen.

With reference now to FIG. 10B, at 1040 the method 1000 may include receiving a reposition input from the user. At 1044 the reposition input from the user may be received from an input device selected from the group consisting of a hand-held mechanically actuatable stylus, a depth camera, a ring, a microphone, and the gaze tracking system. At 1048 the method 1000 may include disabling the gaze tracking system in response to receiving the reposition input. At 1052 the method 1000 may include, in response to receiving the reposition input, using subsequently received head pose data to calculate an adjusted location for the target indicator in the display region.

At 1056 the method 1000 may include receiving secondary tracking data. At 1060 the method 1000 may include, in response to receiving the reposition input, using the secondary tracking data to calculate the adjusted location for the target indicator. At 1064 the method 1000 may include controlling the display device to display the target indicator at the adjusted location in the display region. At 1068 the method 1000 may include not displaying the target indicator until the reposition input is received. At 1072 the method 1000 may include, after the target indicator is displayed at the adjusted location, receiving a selection user input. At 1076 the method 1000 may include, in response to receiving the selection user input, selecting a selectable target located at the adjusted location.

It will be appreciated that method 1000 is provided by way of example and is not meant to be limiting. Therefore, it is to be understood that method 1000 may include additional and/or alternative steps than those illustrated in FIGS. 10A and 10B. Further, it is to be understood that method 1000 may be performed in any suitable order. Further still, it is to be understood that one or more steps may be omitted from method 1000 without departing from the scope of this disclosure.

Figure 11:
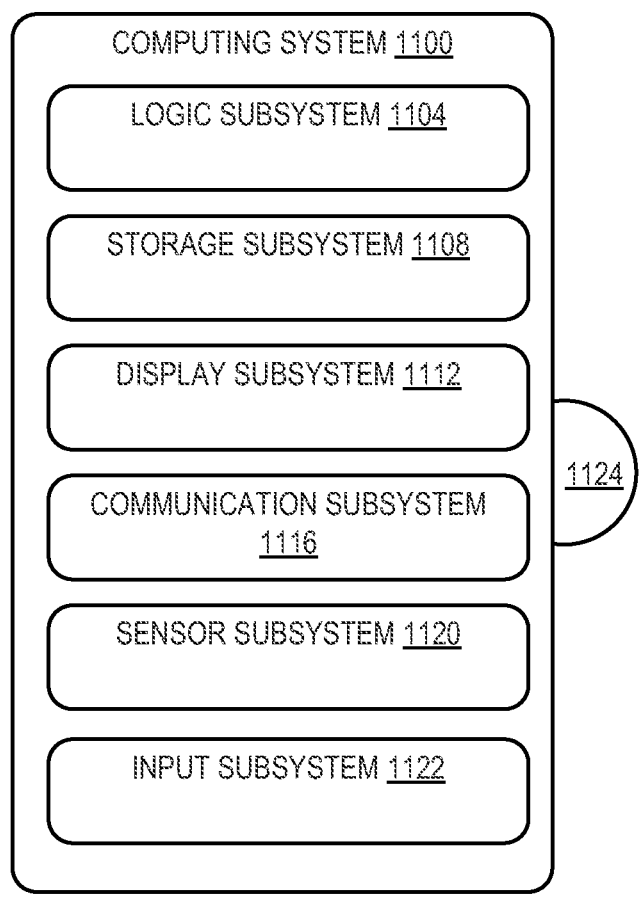
FIG. 11 is a simplified schematic illustration of an embodiment of a computing device.

FIG. 11 schematically shows a nonlimiting embodiment of a computing system 1100 that may perform one or more of the above described methods and processes. Computing device 22 and tablet computer 632 may take the form of computing system 1100. Computing system 1100 is shown in simplified form. It is to be understood that virtually any computer architecture may be used without departing from the scope of this disclosure.

In different embodiments, computing system 1100 may take the form of a mainframe computer, server computer, desktop computer, laptop computer, tablet computer, home entertainment computer, network computing device, mobile computing device, mobile communication device, gaming device, etc. As noted above, in some examples the computing system 1100 may be integrated into a display device, such as the HMD device 50, first wall-mounted display 620 or second wall-mounted display 624.

As shown in FIG. 11, computing system 1100 may include a logic subsystem 1104 and a storage subsystem 1108. In some examples computing system 1100 may also include a display subsystem 1112, a communication subsystem 1116, a sensor subsystem 1120 and/or an input subsystem 1122. Computing system 1100 may also optionally include other subsystems and components not shown in FIG. 11. Computing system 1100 may also include computer readable media, with the computer readable media including computer readable storage media and computer readable communication media. Computing system 1100 may also optionally include other user input devices such as keyboards, mice, game controllers, and/or touch screens, for example. Further, in some embodiments the methods and processes described herein may be implemented as a computer application, computer API, computer library, and/or other computer program product in a computing system that includes one or more computers.

Logic subsystem 1104 may include one or more physical devices configured to execute one or more instructions. For example, the logic subsystem 1104 may be configured to execute one or more instructions that are part of one or more applications, programs, routines, libraries, objects, components, data structures, or other logical constructs. Such instructions may be implemented to perform a task, implement a data type, transform the state of one or more devices, or otherwise arrive at a desired result.

The logic subsystem 1104 may include one or more processors that are configured to execute software instructions. Additionally or alternatively, the logic subsystem may include one or more hardware or firmware logic machines configured to execute hardware or firmware instructions. Processors of the logic subsystem may be single core or multi-core, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Storage subsystem 1108 may include one or more physical, persistent devices configured to hold data and/or instructions executable by the logic subsystem 1104 to implement the herein described methods and processes. When such methods and processes are implemented, the state of storage subsystem 1108 may be transformed (e.g., to hold different data).

Storage subsystem 1108 may include removable media and/or built-in devices. Storage subsystem 1108 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Storage subsystem 1108 may include devices with one or more of the following characteristics: volatile, nonvolatile, dynamic, static, read/write, read-only, random access, sequential access, location addressable, file addressable, and content addressable.

In some embodiments, aspects of logic subsystem 1104 and storage subsystem 1108 may be integrated into one or more common devices through which the functionally described herein may be enacted, at least in part. Such hardware-logic components may include field-programmable gate arrays (FPGAs), program- and application-specific integrated circuits (PASIC/ASICs), program- and application-specific standard products (PSSP/ASSPs), system-on-a-chip (SOC) systems, and complex programmable logic devices (CPLDs), for example.

FIG. 11 also shows an aspect of the storage subsystem 1108 in the form of removable computer readable storage media 1124, which may be used to store data and/or instructions executable to implement the methods and processes described herein. Removable computer-readable storage media 1124 are physical devices that may take the form of CDs, DVDs, HD-DVDs, Blu-Ray Discs, EEPROMs, and/or floppy disks, among others, and hold the data and/or instructions in a persistent manner, for a finite duration.

In contrast, in some embodiments aspects of the instructions described herein may be propagated by computer-readable communications media, such as a communications bus, port, or optical fiber, etc., in a transitory fashion by a pure signal (e.g., an electromagnetic signal, an optical signal, etc.) that is not held by a physical device for at least a finite duration.

When included, display subsystem 1112 may be used to present a visual representation of data held by storage subsystem 1108. As the above described methods and processes change the data held by the storage subsystem 1108, and thus transform the state of the storage subsystem, the state of the display subsystem 1112 may likewise be transformed to visually represent changes in the underlying data. The display subsystem 1112 may include one or more display devices utilizing virtually any type of technology. Such display devices may be combined with logic subsystem 1104 and/or storage subsystem 1108 in a shared enclosure, or such display devices may be peripheral display devices. With reference also to FIGS. 1, 2 and 4, the display subsystem 1112 may include, for example, the display system 14.

When included, communication subsystem 1116 may be configured to communicatively couple computing system 1100 with one or more networks and/or one or more other computing devices. Communication subsystem 1116 may include wired and/or wireless communication devices compatible with one or more different communication protocols. As nonlimiting examples, the communication subsystem 1116 may be configured for communication via a wireless telephone network, a wireless local area network, a wired local area network, a wireless wide area network, a wired wide area network, etc. In some embodiments, the communication subsystem may allow computing system 1100 to send and/or receive messages to and/or from other devices via a network such as the Internet.

Sensor subsystem 1120 may include one or more sensors configured to sense different physical phenomenon (e.g., position, orientation, acceleration, visible light, infrared light, sound, etc.) as described above. Sensor subsystem 1120 may be configured to provide sensor data to logic subsystem 1104, for example. As described above, such data may include gaze tracking information, head pose information, depth tracking information, image information, audio information, ambient lighting information, position information, motion information, user location information, and/or any other suitable sensor data that may be used to perform the methods and processes described above.

When included, input subsystem 1122 may comprise or interface with one or more sensors or user-input devices such as an inertial measurement unit, game controller, gesture input detection device, voice recognizer, keyboard, mouse, or touch screen. In some embodiments, the input subsystem 1122 may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

The term "module" may be used to describe an aspect of the user interface system 10 that is implemented to perform one or more particular functions. In some cases, such a module may be instantiated via logic subsystem 1104 executing instructions held by storage subsystem 1108. It is to be understood that different modules may be instantiated from the same application, code block, object, library, routine, API, function, etc. Likewise, the same module may be instantiated by different applications, code blocks, objects, routines, APIs, functions, etc. The term "module" is meant to encompass individual or groups of executable files, data files, libraries, drivers, scripts, database records, etc.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A head-mounted computing device for positioning a target indicator displayed via a display system, the head-mounted computing device operatively connected to the display system, the head-mounted computing device comprising:
   a gaze tracking system for generating gaze tracking data having a coarse accuracy from a user wearing the head-mounted computing device;
   a head tracking system for generating head pose data from the user, wherein the head pose data has a fine accuracy that is greater than the coarse accuracy of the gaze tracking data; and
   a positioning module executed by a processor of the head-mounted computing device, the positioning module configured to:
      using the gaze tracking data, determine an approximate user gaze region within a display region generated by the display system;
      control the display system to display the target indicator at an initial location within the approximate user gaze region;
      receive a reposition input from the user;
      in response to receiving the reposition input, use subsequently received head pose data to calculate an adjusted location for the target indicator in the display region; and
      control the display system to display the target indicator at the adjusted location in the display region.

2. The head-mounted computing device of claim 1, wherein the positioning module is further configured to:
   after the target indicator is displayed at the adjusted location, receive a selection user input; and
   in response to receiving the selection user input, select a selectable target located at the adjusted location.

3. The head-mounted computing device of claim 1, wherein the reposition input from the user is received from an input device selected from the group consisting of a hand-held mechanically actuatable stylus, a depth camera, a ring, a microphone, and the gaze tracking system.

4. The head-mounted computing device of claim 1, wherein the target indicator is not displayed until the reposition input is received.

5. The head-mounted computing device of claim 1, wherein the positioning module is further configured to, in response to receiving the reposition input, disable the gaze tracking system.

6. The head-mounted computing device of claim 1, wherein the display system comprises a near-eye display system integrated in the head-mounted computing device.

7. The head-mounted computing device of claim 1, wherein the display system comprises a screen in a physical environment and separate from the head-mounted computing device, the head-mounted computing device further comprises an optical sensor for capturing images of the physical environment including the screen, and the positioning module is further configured to:
   use the images to establish a spatial relationship between the head-mounted computing device and the screen; and
   use the spatial relationship in combination with the gaze tracking data to determine the approximate user gaze region within the display region of the screen.

8. The head-mounted computing device of claim 7, wherein the positioning module is further configured to receive a screen identifier from the screen.

9. The head-mounted computing device of claim 1, wherein the positioning module is further configured to:
   receive secondary tracking data; and
   in response to receiving the reposition input, use subsequently received secondary tracking data to calculate the adjusted location for the target indicator.

10. A method for positioning a target indicator displayed via a display system, the method comprising:
   receiving gaze tracking data having a coarse accuracy from a gaze tracking system of a computing device;
   receiving head pose data having a fine accuracy that is greater than the coarse accuracy of the gaze tracking data, the head pose data received from a head tracking system of the computing device;
   using the gaze tracking data, determining an approximate user gaze region within a display region generated by the display system;
   controlling the display system to display the target indicator at an initial location within the approximate user gaze region;

receiving a reposition input from the user;

in response to receiving the reposition input, using subsequently received head pose data to calculate an adjusted location for the target indicator in the display region; and controlling the display system to display the target indicator at the adjusted location in the display region.

11. The method of claim 10, further comprising:

after the target indicator is displayed at the adjusted location, receiving a selection user input; and in response to receiving the selection user input, selecting a selectable target located at the adjusted location.

12. The method of claim 10, wherein the reposition input from the user is received from an input device selected from the group consisting of a hand-held mechanically actuatable stylus, a depth camera, a ring, a microphone, and the gaze tracking system.

13. The method of claim 10, further comprising not displaying the target indicator until the reposition input is received.

14. The method of claim 10, further comprising disabling the gaze tracking system in response to receiving the reposition input.

15. The method of claim 10, wherein the display system comprises a screen integrated in the computing device.

16. The method of claim 10, wherein the display system comprises a screen in a physical environment and separate from the computing device, the computing device further comprises an optical sensor for capturing images of the physical environment including the screen, and the method further comprising:

using the images to establish a spatial relationship between the computing device and the screen; and using the spatial relationship in combination with the gaze tracking data to determine the approximate user gaze region within the display region of the screen.

17. The method of claim 16, further comprising receiving a screen identifier from the screen.

18. The method of claim 10, further comprising:

receiving secondary tracking data; and in response to receiving the reposition input, using the secondary tracking data to calculate the adjusted location for the target indicator.

19. A head-mounted display device for positioning a target indicator displayed via a display system, the head-mounted display device operatively connected to a computing device, the head-mounted display device comprising:

a gaze tracking system for generating gaze tracking data having a coarse accuracy from a user wearing the head-mounted computing device;

a head tracking system for generating head pose data from the user, wherein the head pose data has a fine accuracy that is greater than the coarse accuracy of the gaze tracking data; and a positioning module executed by a processor of the computing device, the positioning module configured to:

using the gaze tracking data, determine an approximate user gaze region within a display region generated by the display system;

receive a reposition input from the user;

in response to receiving the reposition input, control the display system to display the target indicator at an initial location within the approximate user gaze region;

in response to receiving the reposition input, use subsequently received head pose data to calculate an adjusted location for the target indicator in the display region;

control the display system to display the target indicator at the adjusted location in the display region;

after the target indicator is displayed at the adjusted location, receive a selection user input; and in response to receiving the selection user input, select a selectable target located at the adjusted location.

20. The head-mounted display device of claim 19, wherein the reposition input from the user is received from an input device selected from the group consisting of a hand-held mechanically actuatable stylus, a depth camera, a ring, a microphone, and the gaze tracking system.

* * * * *